(12) United States Patent
Chai et al.

(10) Patent No.: US 6,940,073 B1
(45) Date of Patent: Sep. 6, 2005

(54) METHOD FOR DETERMINING THE CONCENTRATION OF HYDROGEN PEROXIDE IN A PROCESS STREAM AND A SPECTROPHOTOMETRIC SYSTEM FOR THE SAME

(75) Inventors: Xin Sheng Chai, Atlanta, GA (US); Jun Yong Zhu, Marietta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 236 days.

(21) Appl. No.: 10/290,702

(22) Filed: Nov. 8, 2002

(51) Int. Cl.⁷ ............................................. G01N 21/33
(52) U.S. Cl. ...................................................... 250/373
(58) Field of Search ........................................ 250/373

(56) References Cited

U.S. PATENT DOCUMENTS

| | | | |
|---|---|---|---|
| 2,617,940 A | | 11/1952 | Giguere |
| 3,183,173 A | | 5/1965 | Oakes |
| 3,595,755 A | | 7/1971 | Hartel |
| 3,962,029 A | | 6/1976 | Wettermark et al. |
| 4,680,271 A | | 7/1987 | Williams |
| 5,139,956 A | | 8/1992 | Schick et al. |
| 5,438,002 A | | 8/1995 | Mallard de la Varende et al. |
| 5,474,938 A | | 12/1995 | Jadesjo et al. |
| 5,715,173 A | * | 2/1998 | Nakajima et al. ........... 700/266 |
| 5,756,358 A | | 5/1998 | Mallard de la Varende et al. |
| 6,023,065 A | * | 2/2000 | Garver, Jr. .................... 250/372 |
| 6,269,680 B1 | * | 8/2001 | Prieve et al. ............... 73/23.21 |
| 6,339,222 B1 | * | 1/2002 | Kester et al. ........... 250/339.09 |
| 6,528,016 B1 | * | 3/2003 | Kohler et al. .................. 422/28 |
| 6,746,647 B2 | * | 6/2004 | Kohler et al. .................. 422/28 |
| 6,774,992 B1 | * | 8/2004 | Garver et al. ................ 356/301 |
| 2003/0025909 A1 | * | 2/2003 | Hallstadius .................. 356/436 |

FOREIGN PATENT DOCUMENTS

| | | |
|---|---|---|
| DE | 198 58 027 | 6/2000 |
| EP | 0 243 126 B1 | 8/1992 |

OTHER PUBLICATIONS

The hydrogen peroxide content of a bleaching solution, KCL Method No. 214:85 (1985).

Damlin & Gustavsson, Residual peroxide measurement—Monitoring the hydrogen peroxide bleaching process, Paper Technology, vol. 40, No. 7, p. 101-107 (1999).

G. Telep & D.F. Boltz, Ultraviolet Spectrophotometric Determination of Molybdenum, Anal. Chem., vol. 22, No. 8, pp. 1030-1031 (1950).

D.B. Moore & D.S. Argyropoulos, Determination of Peroxygen Species Present in Pulp Fiber Matrixes, Anal. Chem. vol. 71, pp. 109-114 (1999).

* cited by examiner

Primary Examiner—Albert Gagliardi
(74) Attorney, Agent, or Firm—Troutman Sanders LLP; Ryan A. Schneider

(57) ABSTRACT

The present invention is directed to a method for determining the concentration of hydrogen peroxide in a chemical process stream which may include interfering components. Still further, this invention is directed to a method and apparatus for the on-line, automated determination and control of hydrogen peroxide in a process stream.

19 Claims, 5 Drawing Sheets

(1) Laboratory Off-line Apparatus for Peroxide Determination

(1) Laboratory Off-line Apparatus for Peroxide Determination

METHOD FOR DETERMINING THE CONCENTRATION OF HYDROGEN PEROXIDE IN A PROCESS STREAM AND A SPECTROPHOTOMETRIC SYSTEM FOR THE SAME

DESCRIPTION OF THE INVENTION

The present invention is directed to a method for determining the concentration of hydrogen peroxide in a chemical process stream. More particularly, the present invention is directed to a method for determining the concentration of hydrogen peroxide in a chemical process stream which may include interfering components. Still further, this invention is directed to a method and apparatus for the on-line, automated determination and control of hydrogen peroxide in a process stream.

Hydrogen peroxide has become a common bleaching agent that is used in a wide variety of commercial process streams. The application of hydrogen peroxide in commercial bleaching processes has lessened the environmental impact of prior chlorine based bleaching processes. Hydrogen peroxide has become a staple bleaching agent for use, for example, in pulp and paper manufacture and in textile manufacture. Control of the concentration of hydrogen peroxide used in these bleaching processes can eliminate issues associated with incomplete bleaching or economic waste. Insufficient hydrogen peroxide results in incomplete bleaching, while excess hydrogen peroxide results in waste.

During pulp manufacture, for example, insufficient residual peroxide can lead to brightness reversion. On the other hand, excess hydrogen peroxide is expensive and results in waste. Therefore, monitoring the hydrogen peroxide concentration in a pulp stream during the pulp bleaching process can result in the The presence and concentration of hydrogen peroxide can be determined using a spectroscopic determination, for example spectroscopy in the visible, ultraviolet (UV) and IR ranges. However, when other compositions are present, these compositions may result in interference making it difficult, or impossible, to measure hydrogen peroxide content. While some interfering compositions can be successfully removed, many can not, and the removal process may be difficult, expensive, or time consuming.

The present invention provides a method for determining the presence and concentration of hydrogen peroxide in a process stream, despite the presence of these interfering compositions. According to one embodiment of the present invention, the concentration of hydrogen peroxide can be measured quickly and easily. According to another embodiment of the invention, the hydrogen concentration can be used to provide an automated response which adjusts the amount of the hydrogen peroxide in the process.

The present invention allows for either on-line or off-line measurement of the concentration of hydrogen peroxide in a process stream. According to both of these embodiments of the invention, the hydrogen peroxide content may be measured in real time making it possible to modify and control the hydrogen peroxide content and thus, control the bleaching process.

According to one embodiment of the present invention, the use of an isosbestic point and the application of a dual wavelength method make it possible to eliminate the spectral interference of interfering compounds. An isosbestic point refers to a wavelength at which a set of solutions with different compositions have the same absorptivity.

The present invention can be used to evaluate and control the hydrogen peroxide content in process streams which have heretofore been difficult to evaluate due to the presence of spectral interfering compositions. Appropriate process streams for use with the present method will be readily apparent to the skilled artisan. A non-exhaustive list of process streams includes pulp bleaching streams, textile bleaching streams, wastewater treatment streams, and other chemical streams that require hydrogen peroxide. While the present invention will be described generally with respect to a pulp bleaching stream, application and adaptation of this method and apparatus to other hydrogen peroxide containing process streams will be readily apparent to the skilled artisan.

According to one embodiment, the method and apparatus of the present invention are used to determine the hydrogen peroxide concentration in a pulp bleaching stream. In the area of pulp process streams, the use of hydrogen peroxide relates to the production of total chlorine free pulps (TCP). Spectral interfering compounds found in pulp bleaching streams include dissolved lignin. Dissolved lignin is not a single composition, per se, but is a combination of related compounds which have similar spectral properties.

Much of the dissolved lignin can be precipitated from the bleaching stream in an acidic medium. However, acidifying the medium does not remove all of the lignin and therefore, does not eliminate all of the spectral interference created by the dissolved lignin. While the method of the present invention can used without removing any of the dissolved lignin, it can also be used to determine the hydrogen peroxide content for a stream where some of the lignin has been eliminated. The dual wavelength method allows for the spectral interference of dissolved lignin from the pulp bleaching stream to be negated in the absorption measurement. Specifically, the isosbestic point allows one to account for the spectral interference from dissolved lignin in the process stream.

Reference will now be made in detail to the embodiments of the invention, examples of which are illustrated in the accompanying drawings. Wherever possible, the same reference numbers will be used throughout the drawings to refer to the same or like parts.

DETAILED DESCRIPTION

Figure 1:
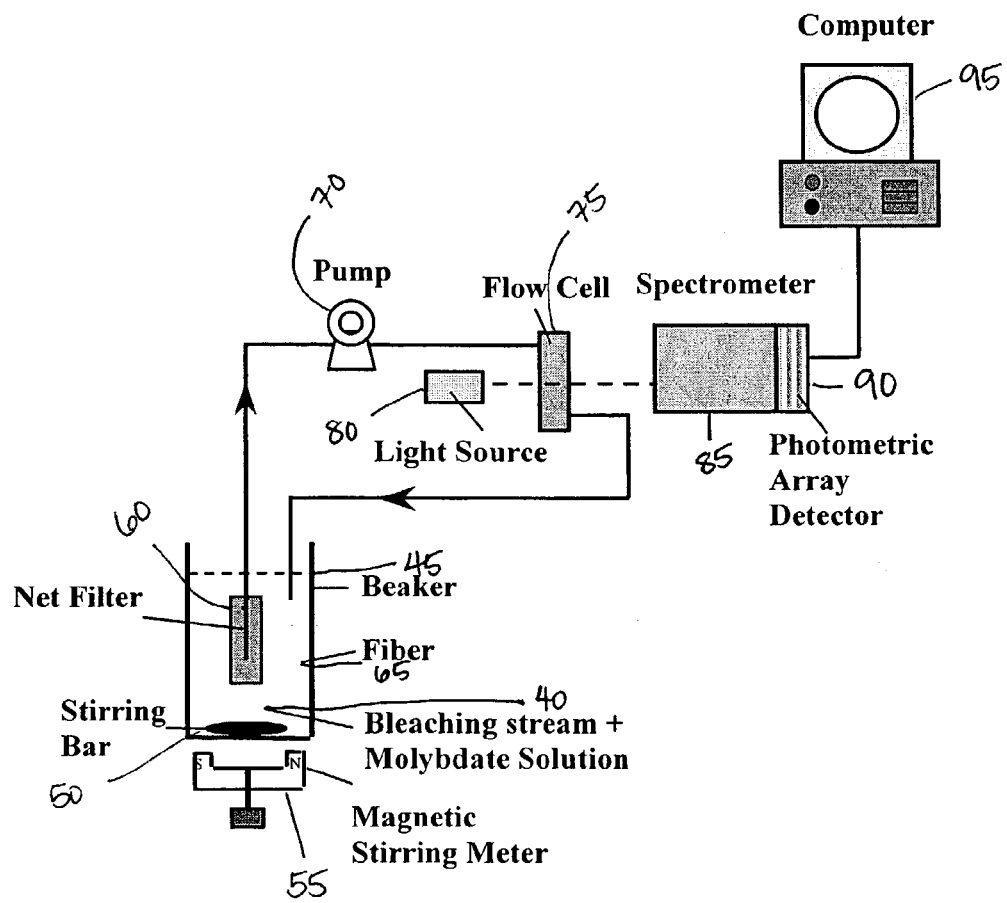
FIG. 1 illustrates an off-line apparatus for hydrogen peroxide determination through UV spectroscopy.

The present invention is directed to a method for determining hydrogen peroxide concentration in a chemical process stream in the presence of at least one interfering compound. At least one interfering compound refers to one or more compounds or complexes with spectral interference.

More particularly, spectral interference refers to interference which can be measured in the visible, infrared, and ultraviolet ranges through spectrophotometry. According to another embodiment of the invention, the chemical process stream to be evaluated for hydrogen peroxide content contains multiple interfering compounds. While the invention will be generally described with reference to a UV system, application of the invention to the visible and IR ranges would be readily apparent to the skilled artisan.

According to one embodiment of the present invention, the concentration of hydrogen peroxide can be determined using a UV spectrophotometric technique based on the reaction of molybdate and hydrogen peroxide that results in a UV absorbing peroxymolybdic complex. Any molybdate salt can be used to introduce the molybdenum to the sample. The most commonly used molybdenum salt is ammonium molybdate; however, other forms of molybdate salt, such as but not limited to, potassium molybdate, sodium molybdate, or chromium molybdate can be used.

First, a sample is taken from the process stream for analysis. The sample may be removed from the stream or accessed, by, for example, an automated sensor. This composition of the sample should be representative of the overall composition of the chemical stream, or that section of the process stream that is of interest. One skilled in the art will recognize that the sample can be taken at any point in the process at which it is decided to measure the hydrogen peroxide. For example, hydrogen peroxide content can be measured at the end of the process to ascertain the residual peroxide content prior to disposal of any portion of the bleaching stream.

The size of the sample can vary and will be readily apparent to the skilled artisan based upon the anticipated content of hydrogen peroxide and the measurement apparatus that is being used. When using an off-line method, if the anticipated concentration of hydrogen peroxide is low, then a larger sample should be removed from the process stream to increase the amount of hydrogen peroxide present in the sample. Likewise, if the anticipated concentration of hydrogen peroxide is high, then a smaller sample should be removed from the process stream.

When using an on-line process, the concentration of hydrogen peroxide should fall within a measurable range. A measurable range of concentrations includes the range recognized by a standard spectrophotometer, i.e., the range in which the concentration is not too low to be detected by the spectrophotometer nor is the sample too concentrated to be measured. If the sample extracted is too concentrated or too dilute, then the sample or sample size would need to be modified. Appropriate methods for modification would be readily apparent to one skilled in the art, and would include diluting or concentrating the sample, respectively.

The sample can be removed from the process stream, for example, in an off-line determination. In an off-line measuring system, the sample is taken from the process stream using any art recognized method, including, but not limited to a valve, tap, or spout. In an off-line measuring system, the sample is usually taken at the end of the bleaching process; however, the sample can be taken at any point in the process at which it is decided to measure the concentration of hydrogen peroxide.

According to one embodiment of the present invention, the sample should be kept at a constant temperature after the sample is removed from the chemical process stream. The temperature at which the sample is processed is not critical and can be any temperature in the range between which the sample freezes or vaporizes. According to one embodiment of the present invention, the sample is cooled. According to another embodiment, the sample is maintained at a constant cooled temperature. Appropriate cooling methods and systems will be readily apparent to the skilled artisan. Any cooling mechanism can be used with the present invention and the cooling system can preferably maintain a constant temperature.

The molybdate solution is added to the sample. The amount of molybdate solution necessary will be based upon the sample size and anticipated concentration of hydrogen peroxide. Thus, one skilled in the art could, based upon knowledge of the stream to be tested and the known reaction of hydrogen peroxide and molybdate to form the colorimetic peroxymolybdic acid complex, select an appropriate amount and concentration of molybdate solution. According to one embodiment of the present invention, an excess of molybdate solution is added to the hydrogen peroxide containing stream or sample. The addition of the molybdate results in its reaction with the hydrogen peroxide to form a peroxymolybdic acid compound. Through the addition of an excess of molybdate, the amount of peroxymolybdic acid complex formed in the aqueous solution is substantially proportional to the amount of hydrogen peroxide in the sample compound.

The amount of molybdate solution that should be added to the sample depends upon the anticipated concentration of hydrogen peroxide in the sample and the size of the sample taken from the process stream. The molybdate solution added to the sample creates an independent absorption in the same spectrum as the peroxymolybdate complex. Therefore, measuring the concentration of hydrogen peroxide requires that the spectral interference from the molybdate be negated. Thus, according to one embodiment of the present invention, the molybdate solution is added at a concentration that is below the saturation level. Thus, while any amount of excess molybdate can be used, since the baseline absorption of the molybdate can interfere with the measurement of the concentration of the hydrogen peroxide, the concentration of the molybdate solution should not go too high, i.e., about the saturation level.

Regardless of which system of measurement is chosen, the instrument must be calibrated before the absorption of the sample can be measured. The instrument can be calibrated with any known reagent for calibration that is available from commercial sources and would be readily apparent to a skilled artisan.

FIG. 1 illustrates one embodiment of the present invention. FIG. 1 illustrates an off-line system for determining the concentration of hydrogen peroxide. According to this embodiment, a sample [40] is first removed from a chemical process stream (not shown). After removal, the sample [40] is placed in a receptacle with stirring. According to the embodiment shown in FIG. 1, the sample is placed in a beaker [50] and stirring is undertaken with a stirring bar [50] and a magnetic stirring meter [55]. Stirring can be carried out with any art recognized stirring means. Appropriate stirring systems will be readily apparent to the skilled artisan.

According to the embodiment shown in FIG. 1, a net filter [60] is submerged in the solution, allowing the sample to be removed from the beaker by a pump [70]. The filter must be used to prevent the fiber [65] present in the process sample from entering the pump.

According to the embodiment shown in FIG. 1, the sample is then be passed through a flow cell [75] that is illuminated from behind by a light source to a spectrophotometer [85]. The spectrophotometer then measures the absorption of the sample from the light stream at two wavelengths, e.g., approximately 297 nm and approximately 350 nm.

Any art recognized spectrophotometer can be used. The spectrophotometer chosen should be capable of measuring an aqueous solution in a range of about 250–500 nm. Appropriate spectrophotometers for use in the present invention includes, for example HP-8452 and other variations that would be readily available to one skilled in the art. The photometric array detector [90] is an integral part of current commercial spectrophotometers.

After the sample spectral absorbencies have been measured, this information should be transmitted to a computer [95] for the calculation of the amount of hydrogen peroxide in the chemical process stream. Adjustments in hydrogen peroxide content can be controlled manually based upon this information or may be fed to a control system for adjusting the hydrogen peroxide addition amounts. If the calculation shows that the concentration of hydrogen peroxide in the process stream is too high, the intake amount of the hydrogen peroxide should be reduced.

Figure 2:
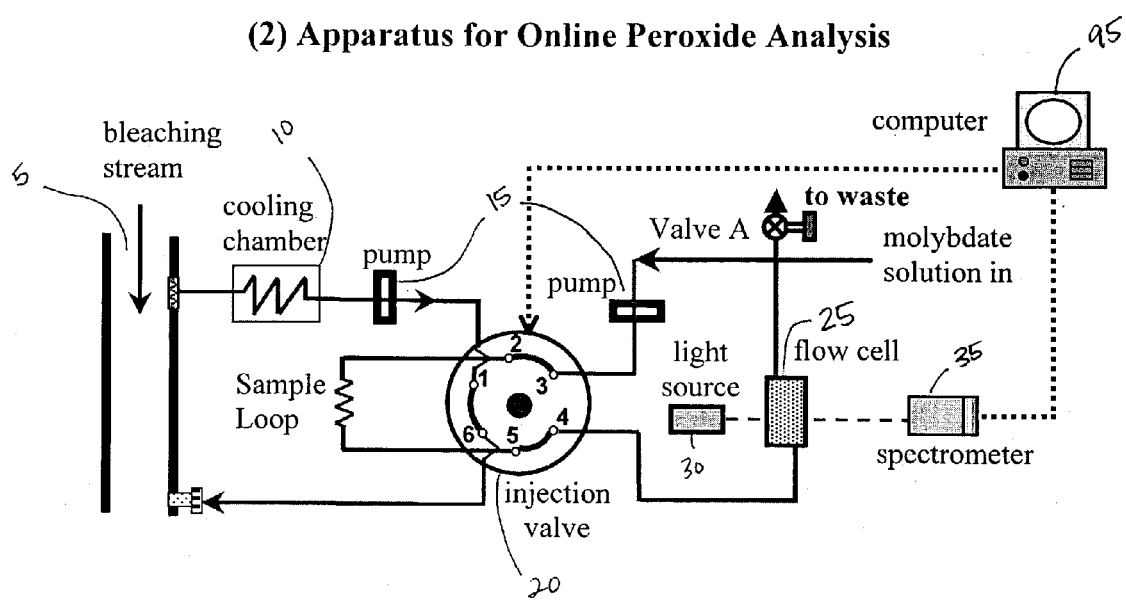
FIG. 2 illustrates an apparatus for on-line hydrogen peroxide determination through UV spectroscopy.

FIG. 2 illustrates another embodiment of the present invention. As depicted in FIG. 2, an on-line detection system may be used to sample and evaluate a chemical process stream [5]. The on-line system is integrated directly into the manufacturing process and is capable of either sampling upon command or continuously.

According to one embodiment of the present solution, after the sample is removed from the process stream, the sample is transferred to a cooling chamber [10]. Appropriate cooling methods and systems will be readily apparent to the skilled artisan. Any cooling mechanism that can cool the sample, preferably to a constant temperature, can be used. According to the embodiment shown in FIG. 2, once the sample has been cooled, the sample is removed from the cooling chamber by a pump [15] that removes the sample to the sample loop of an injection valve [20]. Any pump that is capable of removing the removing the sample from cooling chamber and transporting it to the injection valve can be used. Appropriate pumps will be readily apparent to a skilled artisan.

According to one embodiment of the present solution, the sample in the sample loop can be injected into the molybdate solution. Appropriate injection valves will be readily apparent to the skilled artisan. After the sample is combined with the molybdate solution, the sample is transferred to a flow cell [25] by a second pump [15], where it is irradiated with a light source [30] to a spectrophotometer [35]. The spectrophotometer should then measure the absorption of the sample from the light stream at two wavelengths, such as 297 nm and 350 nm. A standard spectrophotometer should be used, such as the HP-8452 and other variations that would be readily available to one skilled in the art. The spectrophotometer should be chosen based upon the analysis to be undertaken on the stream to be evaluated and may be chosen from a spectrophotometer capable of measuring the absorption of an aqueous stream in ultraviolet, visible and infrared spectrophotometry.

After the measurement of the sample has been taken, this information should be transmitted from the spectrophotometer to a computer [95]. This computer can be connected to the hydrogen peroxide dosing system that controls the amount of hydrogen peroxide that is added to the process stream. By concurrently automating the dosing system and the hydrogen peroxide analysis, a closed-loop system for modifying the amount of hydrogen peroxide added to the stream can be created. Thus, the concentration of hydrogen peroxide can be kept within a desired range.

After the sample passes through the flow cell and the absorption measurements have been taken, the sample can be discarded.

Another embodiment of the present invention involves the method of measuring the absorption of the chemical process stream at two wavelengths. The absorption of the sample should be taken at the isosbestic point and at a wavelength where the concentration of hydrogen peroxide can be measured. Still further, the present invention involves measuring the absorption of the chemical process stream at between about 300 and about 450 nm and at between about 292 and about 302 nm. These wavelengths should be compared to eliminate spectral interference of additional compounds dissolved in the process stream. This comparison is done using the dual wavelength method, which will be discussed infra.

The absorption of the sample should be taken at two wavelengths. The isosbestic point occurs at the wavelength in which the absorption of different compositions is constant regardless of a change in concentration. The isosbestic point for hydrogen peroxide and molybdate systems occurs between 292 and 302 nm.

Figure 3:
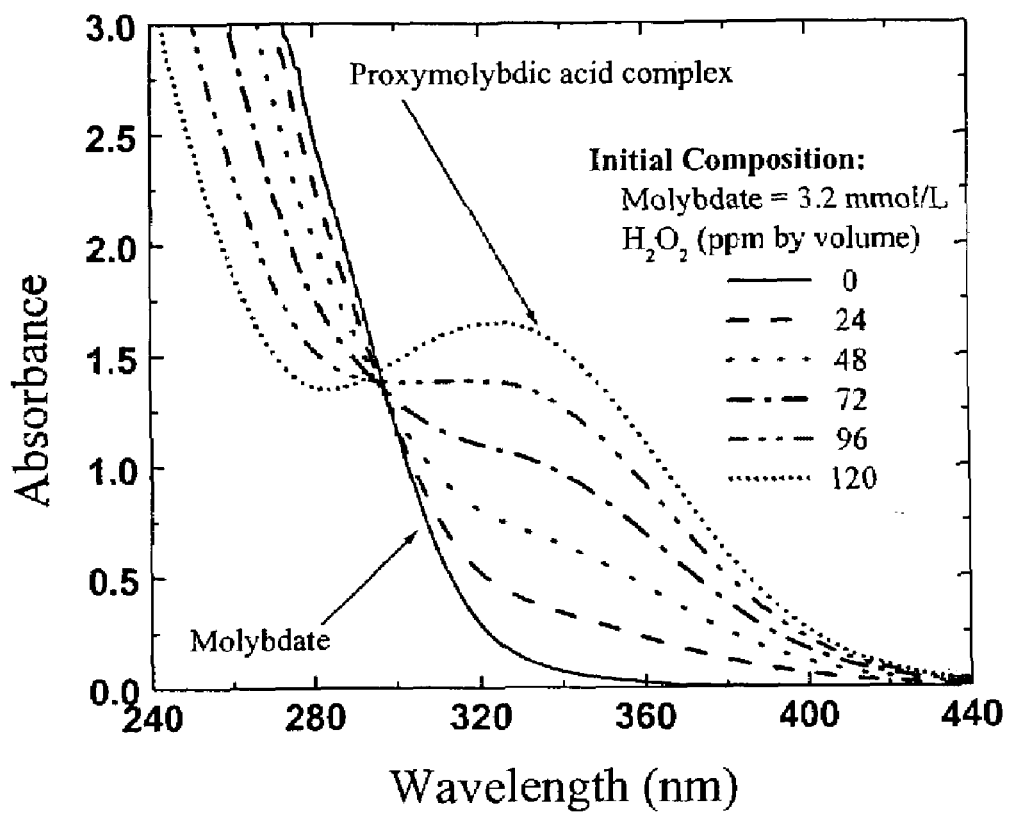
FIG. 3 plots the absorption of molybdate versus the concentration of peroxymolybdate and illustrates the isosbestic point.

Molybdate ions exhibit a strong spectral absorption in the UV range, as shown by FIG. 3. The range of the absorption overlaps the range exhibited by the peroxymolybdate complex; therefore, measuring the concentration of hydrogen peroxide requires the negation of the spectral interference from the molybdate. To eliminate spectral interference from molybdate, the second measurement should be taken at a wavelength where the absorption of molybdate can be negated, which occurs at wavelengths longer than 330 nm.

Once the measurements have been made, the measured absorptions must be compared to eliminate the spectral effect of interfering compounds found in the chemical stream. The dual wavelength method allows for the strong spectral interference from dissolved lignin in the process to be removed and the concentration of hydrogen peroxide to be determined. The dual wavelength method is demonstrated by the following example:

$$C = \frac{k_1}{V_{sample}}[k_3 A_X - k_2(k_3 A_Y - A_Y^o) - A_X^o]$$

In this equation, C is the concentration of hydrogen peroxide (in g/L) and $V_{sample}$ is the sample volume (mL) added into the molybdate solution. The variables $A_x$ and $A_y$ represent the absorption of peroxymolybdate complex and the isosbestic point, respectively. The variables $A^o_x$ and $A^o_y$ represent the absorption measurements of the molybdate solution before the sample was added at X and the isosbestic point, respectively. The calibration constant, $k_1$, can be obtained by plotting the absorption of molybdate at 350 nm against a concentration range of hydrogen peroxide in a molybdate solution, as demonstrated by FIG. 4. The correction factor $k_2$ can be obtained by calculating the average ratio of $A_x/A_y$, as demonstrated by Table II infra. The dilution factor, $k_3$, is used to correct for the dilution of the testing solution when the bleaching stream sample is added into the molybdate solution. If the volume of the molybdate solution was $V_{molyb}$, then the following equation can be used to calculate $k_3$:

$$k_3 = \frac{V_{molyb}}{V_{molyb} + V_{sample}}$$

Another embodiment of the present invention involves the on-line determination of the concentration of hydrogen peroxide in a chemical process. This embodiment involves a means for removing the sample from the chemical process stream; means for determining the absorption of the sample; and means for determining the concentration of hydrogen peroxide in said sample. Means for removing the sample can include any means recognized by one skilled in the necessary art, not to be limited by, but including any pump means, which can be injection, vacuum pumps, and any other pump that will be readily apparent to a skilled artisan.

EXAMPLE

A 3% of hydrogen peroxide, analytical grade, was used as standard for the calibration obtained from Aldrich Ref. 32. 338-1. The amount of hydrogen peroxide in the standard solution was obtained by titration using the KCL method. A color agent, 2 mmol/L $(NH_4)_2MoO_4$ solution was prepared by dissolving 0.10 grams of $(NH_4)_2MoO_4$ in 250 mL 0.5 M $H_2SO_4$.

The hydrogen peroxide content in a bleaching solution or pulp slurry was determined using a titration method known as the KCL Method. A sample of pulp was obtained from the discharge of a peroxide tower prior to neutralization of the discharge with $SO_2$ and the consistency of the pulp sample was determined. A sufficient sample of the pulp was then placed in a Buchner and approximately 100 mL of effluent was collected. Twenty-five mL. of the effluent was pipetted into a 250 mL Erlenmeyer flask. Approximately 10–15 mL of 25% $H_2SO_4$, 5 mL KI solution, and 3 drops of saturated ammonium molybdate solution were added to the flask. The sample was then titrated using 0.1N thiosulfate until the solution demonstrated a pale yellow color. Once the pale yellow color appeared, ten mL of starch solution purchased from Aldrich Ref. 17. 993-0, was added to the sample until the blue color disappeared.

Five sample liquors, three samples from the beginning of the process, shortly after the hydrogen peroxide was introduced, and two samples from the end of the process, after bleaching, were taken. A sample liquor was also taken from the end of the oxygen delignification process, without the addition of hydrogen peroxide, for use in testing the effect of the dissolved lignin.

The starting pressure of oxygen applied to the process was 60 psi. The starting liquor contains 1.27% sodium hydroxide, 0.05% magnesium sulfate, and 0.5% hydrogen peroxide and a 10% pulp consistency. The total process was 55 minutes. The pressure of oxygen in the system continuously decreased to 0 psi atmospheres at the end of the process. The reaction temperature was kept constant at 700° C. A sample liquor from the end of the oxygen delignification process, without adding hydrogen peroxide, was used for the dissolved lignin effect testing.

A spectrophotometer, the HP-8452, Hewlett-Packard, now Agilent Technologies, CA, USA, equipped with a 1-cm cell was used to conduct the experiment. The instrument was calibrated by preparing a set of standard solutions, by adding 2, 4, 8, 12, 16, and 20 $\mu L$ of standard hydrogen peroxide solution (3%) in a 5 mL ammonium molybdate solution. The absorption of each solution was measured at 350 nm using the 1-cm cell. Distilled water was used as a blank in the UV measurement.

Five samples, in three sample sizes, were taken from the prepared bleaching process liquors by micro-syringe. Two samples contained 500 $\mu L$, one sample contained 100 $\mu L$, and two samples contained 10 $\mu L$. Each of these samples were added to the 5 mL molybdate reaction solution and stirred by hand.

The resulting solutions were filtered and their absorbencies were measured at wavelengths of 297 nm and 350 nm. FIG. 3 is a graphical representation of the measured absorbencies of the solutions versus their wavelengths. The graph reveals that the absorbance of the molybdate solution was constant at 297 nm independent of changes in the concentration of hydrogen peroxide. This graph also revealed that the absorption of molybdate was negligible at wavelengths longer than 330 nm.

Figure 4:
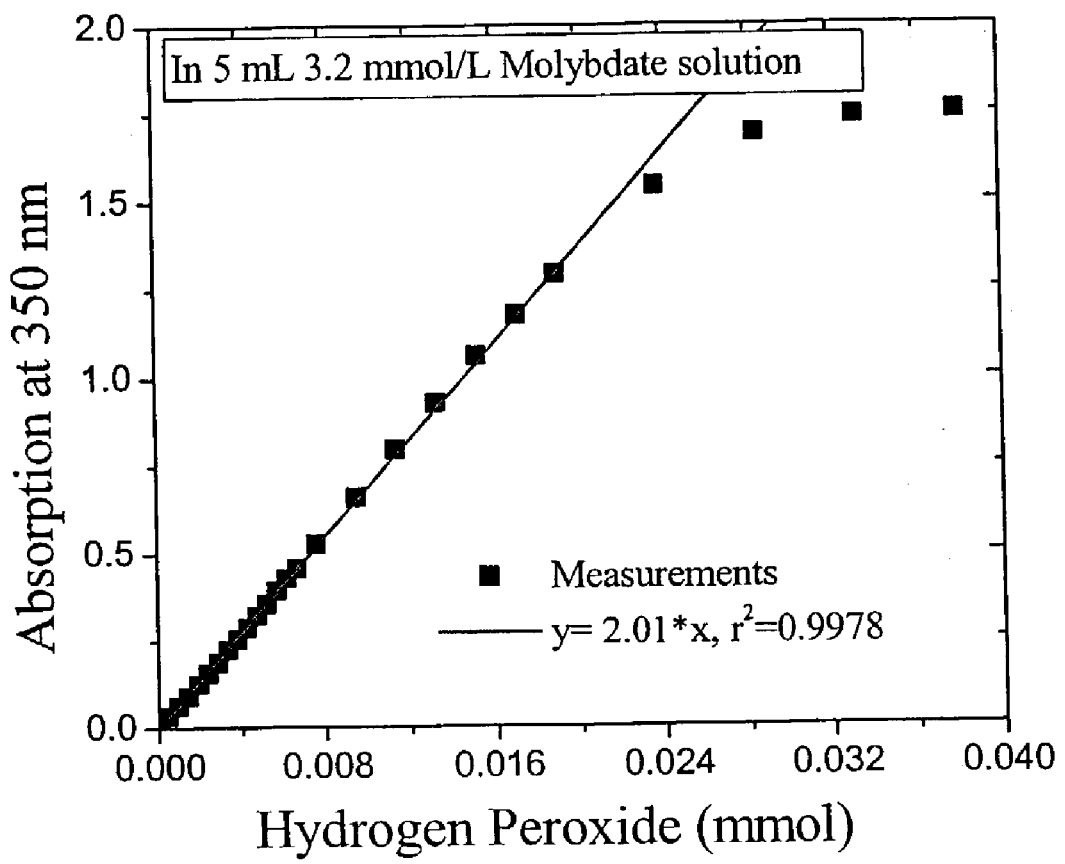
FIG. 4 plots the absorption of molybdate at 350 nm versus a concentration range of hydrogen peroxide from 0 to 0.12 g/L under a molybdate concentration of 3.2 mmol/L.

The measured absorption spectral intensity at 350 nm was plotted against a range of 0 to 0.12 g/L under a molybdate concentration of 3.2 mmol/L, as depicted by FIG. 4. This graph shows a linear relationship between the measured absorption and the known peroxide concentration up to a peroxide concentration up to 0.8 g/L. A nonlinear relationship was exhibited after a concentration of 0.8 g/L, the nonlinear relationship that occurred in concentrations over 0.8 g/L was attributed to the excess of hydrogen peroxide added to the solution.

The concentration of hydrogen peroxide in the sample was calculated using Beer's law. (Beer's law could be used to calculate the hydrogen peroxide content because no interfering components were present in the prepared sample that created spectral interference that needed to be removed.) The concentration of hydrogen peroxide can be calculated using the following equation.

$$C = \frac{k_1}{V_{sample}} A_X$$

where C represents the concentration of hydrogen peroxide (in g/L) and V represents the sample volume (mL) added into the 5 mL molybdate solution. $A_{350}$ represents the absorption reading at 350 nm. The calibration constant, $k_1$, was calculated from the calibration data shown in FIG. 4.

The method described in this example was validated by the titration method as a reference method. Table I compares the data obtained by the present method and the titration method. This comparison indicates that the present method provided results similar to the results that were obtained by the titration method for a sample in the measurable concentration range of hydrogen peroxide. However, samples with extremely low hydrogen peroxide content were shown to produce a relative deviation compared to the titration method of up to 10%.

TABLE I

Comparisons of measured peroxide in bleaching solution using the reference method and the present method

| Sample ID | Sample size (ul) | Hydrogen peroxide, g/L Titration method | Present Method | RSD, % |
|---|---|---|---|---|
| 1* | 500 | 0.019 | 0.017 | −10.5 |
| 2* | 500 | 0.051 | 0.055 | 7.5 |

TABLE I-continued

Comparisons of measured peroxide in bleaching solution using the reference method and the present method

| Sample ID | Sample size (ul) | Hydrogen peroxide, g/L | | RSD, % |
|---|---|---|---|---|
| | | Titration method | Present Method | |
| 3 | 100 | 3.23 | 3.22 | −0.3 |
| 4 | 10 | 20.8 | 21.4 | 2.9 |
| 5 | 10 | 31.7 | 32.4 | 2.2 |

*The sample solutions were from an oxygen delignification process, where only small amounts of hydrogen peroxide are used.

The nonlinear curve exhibited in FIG. 4 at concentrations beyond 0.8 g/L was caused by the excess of hydrogen peroxide added to the solution, which was not reacted to form the peroxymolybdic complex due to the lack of molybdate. As described in this curve, the molar ratio of peroxide to molybdate in the peroxymolybdic complex is 1:2.

Figure 5:
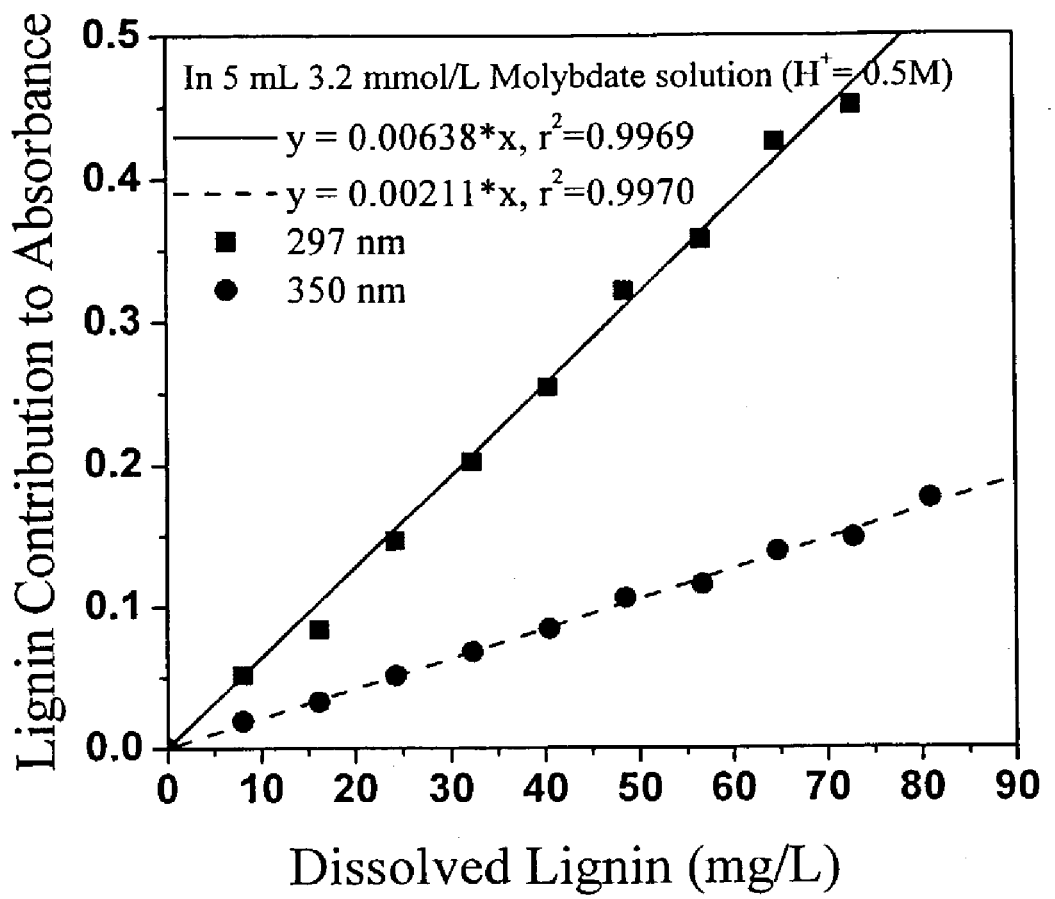
FIG. 5 plots absorbance versus the volume of the oxygen delignification liquor added in a 5 mL, 3.2 mM molybdate solution and illustrates the effect of dissolved lignin on absorption.

Dissolved lignin was added to the molybdate solution to study the effect of the dissolved lignin on absorption. FIG. 5 is a graphical representation of the absorption measured at the two interest wavelengths, 297 nm and 350 nm, versus the volume of the oxygen delignification liquor added in a 5 mL 3.2 mM molybdate solution. The ratio of the absorptions at these two wavelengths, $A_x/A_y$, was constant with a standard deviation of 6.78%, as listed in Table 11, which illustrates in tabular form the spectral absorption contributed by dissolved lignin at the two interest wavelengths. This constant relationship between the absorptions was found to be independent of the amount of lignin added. Therefore, it was determined that the spectral contribution of lignin at 297 nm was used to correct for spectral interference at 350 nm by lignin.

TABLE II

Spectral absorption contributed from dissolved lignin at 297 and 350 nm*

| Sample No. | Net absorbance at 297 nm | Net absorbance at 350 nm | Ratio of $A_{350}/A_{297}$ |
|---|---|---|---|
| 1 | 0.0513 | 0.0193 | 0.376 |
| 2 | 0.0839 | 0.0327 | 0.389 |
| 3 | 0.1464 | 0.0513 | 0.350 |
| 4 | 0.2020 | 0.0681 | 0.337 |
| 5 | 0.2541 | 0.0844 | 0.332 |
| 6 | 0.3215 | 0.1057 | 0.323 |
| 7 | 0.3573 | 0.1154 | 0.323 |
| 8 | 0.4258 | 0.1384 | 0.325 |
| 9 | 0.4507 | 0.1479 | 0.328 |
| 10 | 0.5268 | 0.1757 | 0.334 |
| Average | | | 0.342 |
| RSTD | | | 6.78% |

*An sample liquor from oxygen delignification process (no hydrogen peroxide) is used in the study. The content of dissolved lignin is this sample is 40.3 g/L, 10–100 µL sample was added into 5 mL 3.2 mM molybdate solution for the testing.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method of determining the hydrogen peroxide concentration of a chemical process stream containing at least one interfering component comprising:

adding to said chemical process stream containing hydrogen peroxide, a molybdate solution, wherein said solution contains an excess of molybdate ions, measuring by UV spectroscopy, the absorption at wavelength at or between about 300 and about 450 nm (Absorption A) and at or between about 292 to about 302 nm (Absorption B); and determining the concentration of hydrogen peroxide by comparing the two absorption measurements.

2. The method according to claim 1, wherein the molybdate solution has a concentration of less than about 3.2 mmol/L.

3. The method according to claim 1, wherein the absorption (Absorption A) is measured between about 330 and 375 nm.

4. The method according to claim 1, wherein the absorption (Absorption 8) is measured at between about 294 and 300 nm.

5. The method according to claim 1, wherein said chemical process stream is an aqueous stream.

6. The method according to claim 4, wherein said chemical process stream is at least one of 4 pulp or paper processing stream, a wastewater stream, or a textile bleaching stream.

7. The method according to claim 1, wherein the chemical process stream is a pulp stream and the at least one interfering component is chosen from dissolved lignin.

8. The method according to claim 1, wherein said chemical process stream is a pulp or paper process stream and wherein the stream first is treated in an acidic medium to precipitated dissolved lignin.

9. The method according to claim 1, wherein the molybdate solution is produced comprising an ammonium salt of molybdenum.

10. The method according to claim 1, wherein the two absorption measurements are compared by the following equation:

$$C = \frac{k_1}{V_{sample}} [k_3 A_X - k_2(k_3 A_Y - A_Y^o) - A_X^o]$$

wherein C is the concentration of hydrogen peroxide (in g/L) $V_{sample}$ is the sample volume in (mL), $A_x$ and $A_y$ represent the absorption of peroxymolybdate complex and the isosbestic point, respectively, wherein the variables $A^o_x$ and $A^o_y$ represent the absorption measurements of the molybdate solution before the sample was added at X and the isosbestic point, $k_1$, is a calibration constant, $k_2$ is a correction factor, and $k_3$ is a dilution factor.

11. The method according to claim 1, wherein the concentration of hydrogen peroxide in said process stream is changed in response to said determination.

12. An on-line system for measuring hydrogen peroxide concentration of a chemical process stream containing at least one interfering component comprising:

means for removing a sample from said chemical process stream;

means for determining the UV adsorption of said sample at least two wavelengths;

means for determining the concentration of hydrogen peroxide in said chemical process stream; and a means for introducing a molybdate solution to said sample.

13. The system according to claim 12, wherein said means for removing a sample is a pump.

14. The system according to claim 12, further comprising cooling means for cooling said sample prior to measuring the UV adsorption.

15. The system according to claim 12, wherein said means for determining the UV adsorption is a UV spectrometer.

16. The system according to claim 15, wherein said means for determining the UV adsorption further comprises a light source.

17. The system according to claim 16, wherein the sample is passed through a flow cell between said UV spectrometer and said light source.

18. The system according to claim 12, wherein said means for determining the concentration of hydrogen peroxide is a computer.

19. An on-line system for measuring hydrogen peroxide concentration of a chemical process stream containing at least one interfering component comprising:
- means for removing a sample from said chemical process stream;
- means for determining the UV adsorption of said sample at least two wavelengths;
- means for determining the concentration of hydrogen peroxide in said chemical process stream; and
- a means for introducing a molybdate solution to said sample;
- wherein said means for introducing a molybdate solution to said sample is an injection valve.

* * * * *